US00PP34937P2

(12) United States Plant Patent
Rietberg

(10) Patent No.: US PP34,937 P2
(45) Date of Patent: Jan. 24, 2023

(54) ***HEBE* PLANT NAMED 'HL1802019'**

(50) Latin Name: ***Hebe* hybrid**
Varietal Denomination: HL1802019

(71) Applicant: Henrik Christiaan Cozijn Rietberg, Wezep (NL)

(72) Inventor: Henrik Christiaan Cozijn Rietberg, Wezep (NL)

(73) Assignee: EDEN'S CREATIONS B.V., Wezep (NL)

( * ) Notice: Subject to any disclaimer, the term of this patent is extended or adjusted under 35 U.S.C. 154(b) by 0 days.

(21) Appl. No.: 17/743,882

(22) Filed: May 13, 2022

(51) Int. Cl.
*A01H 5/02* (2018.01)
*A01H 6/68* (2018.01)

(52) U.S. Cl.
USPC ..... Plt./226
CPC ..... *A01H 6/68* (2018.05)

(58) Field of Classification Search
USPC ..... Plt./226, 251
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hebe* plant named 'HL1802019' that characterized by its consistently healthy plants that have a low susceptibility to leaf spot disease and downy mildew, its compact plant habit, its leaves that are small in size, its flowers that are intense violet-purple in color, and its floriferous blooming habit.

2 Drawing Sheets

Botanical classification: *Hebe* hybrid.
Cultivar designation: 'HL1802019'.

CROSS REFERENCE TO A RELATED APPLICATION

This application is related to a European plant breeders' rights application filed on Sep. 15, 2020, application No. 2020/2167. The Applicant received the information for the Plant breeders' rights application directly from the Inventor.

BACKGROUND OF THE INVENTION

The present invention relates to a new and distinct cultivar of *Hebe*, botanically of hybrid origin, known as *Hebe* 'HL1802019' and will be referred to hereafter by its cultivar name, 'HL1802019'. 'HL1802019' is an evergreen shrub grown for use as a container plant and as a landscape shrub.

The new cultivar was derived from a controlled breeding program conducted by the Inventor in Wezep, The Netherlands. The goal of the breeding program is to select new cultivars of *Hebe* with improved plant health, compact plant habits, small leaves, abundant flowering, and self-cleaning flowers. The new cultivar arose from a cross made in September of 2017 between an unnamed and unpatented proprietary plants from the Inventor's breeding program; reference no. HM17-305 as the female parent and ref no. PM17-206 as the male parent. The Inventor selected 'HL1802019' in September of 2018 as a single unique plant amongst the seedlings that resulted from the above cross.

Asexual propagation of the new cultivar was first accomplished by stem cuttings in September of 2018 by the Inventor in Wezep, The Netherlands. Asexual propagation by stem cuttings and tissue culture using meristematic tissue has determined the characteristics of the new cultivar are stable and reproduced true to type in successive generations.

SUMMARY OF THE INVENTION

The following traits have been repeatedly observed and represent the characteristics of the new cultivar, which in combination distinguish 'HL1802019' as a new and distinct cultivar of *Hebe*.

1. 'HL1802019' exhibits consistently healthy plants that have a low susceptibility to leaf spot disease and downy mildew.
2. 'HL1802019' exhibits a compact plant habit.
3. 'HL1802019' exhibits leaves that are small in size.
4. 'HL1802019' exhibits flowers that are intense violet-purple in color.
5. 'HL1802019' exhibits a floriferous blooming habit.

The female parent of 'HL1802019' differs from 'HL1802019' in having a less compact plant habit, flowers that are less intense purple in color with less uniform blooming and in being less floriferous. The male parent of 'HL1802019' differs from 'HL1802019' in having more susceptibility to leaf spot disease and downy mildew, a more vigorous growth habit, flowers that are less intense purple in color, and leaves that are lighter green in color. 'HL1802019' can be most closely compared to the cultivars 'H130011' and 'Mohawk' (both un-patented). 'H130011' is similar to 'HL1802019' in flower and foliage coloration. 'H130011' differs from 'HL1802019' in having a less compact plant shape and in being less floriferous. 'Mohawk' is similar to 'HL1802019' in leaf size and in having a floriferous blooming habit. 'Mohawk' differs from 'HL1802019' in having more susceptibility to leaf spot disease and downy mildew, lighter green leaves, inflorescences that are slightly longer (more stretched) and are more pointed in shape, and flowers that are slighter lighter purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by All-Blooms, Vida-Verde, Floraxchange, hamiplant, and ozplanten.

BRIEF DESCRIPTION OF THE DRAWINGS

The accompanying color photographs illustrate the overall appearance and distinct characteristics of the new *Hebe*. The photographs were taken of a 7-month-old plant of 'HL1802019' as grown outdoors in a 12-cm container in Wezep, The Netherlands.

The photograph in FIG. 1 is a side view of 'HL1802019' in bloom.

Figure 1:
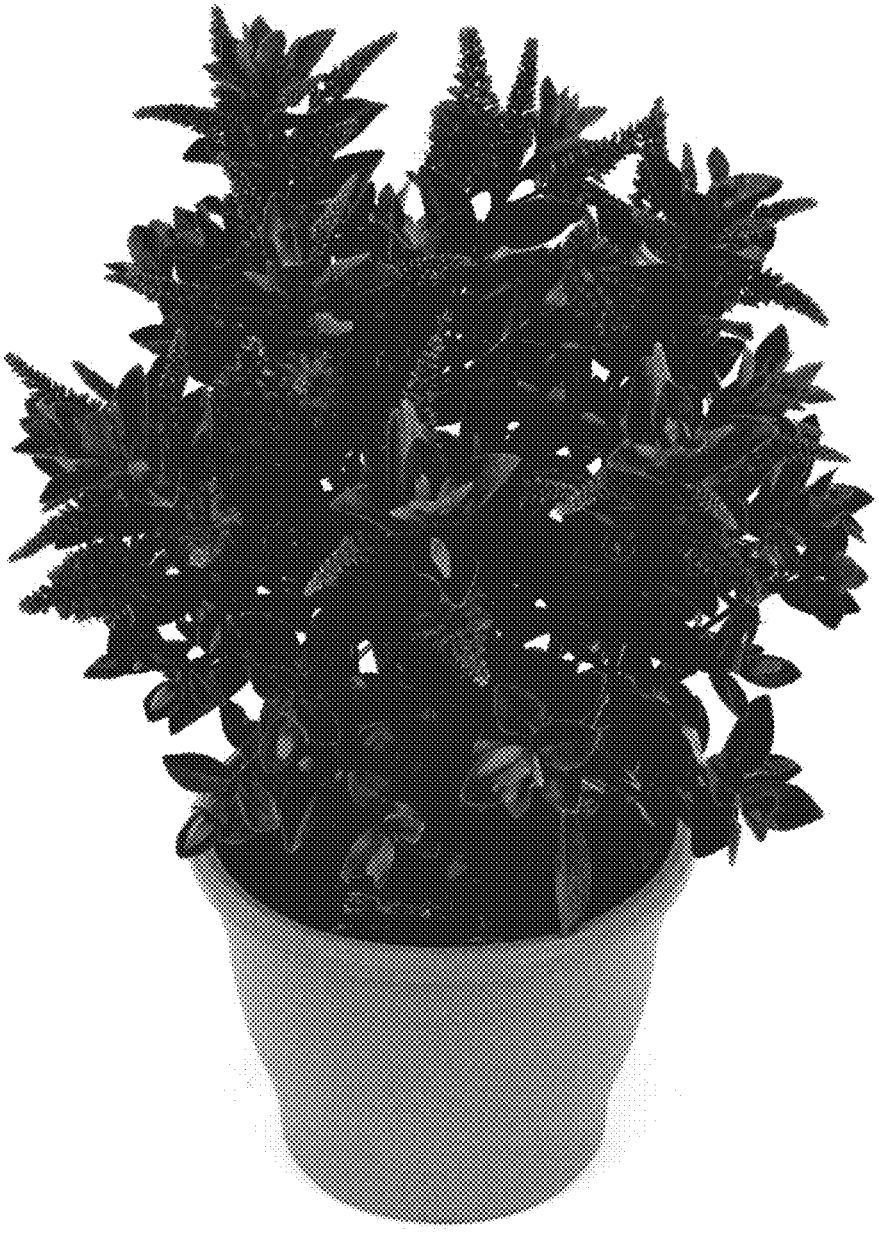
Figure 2:
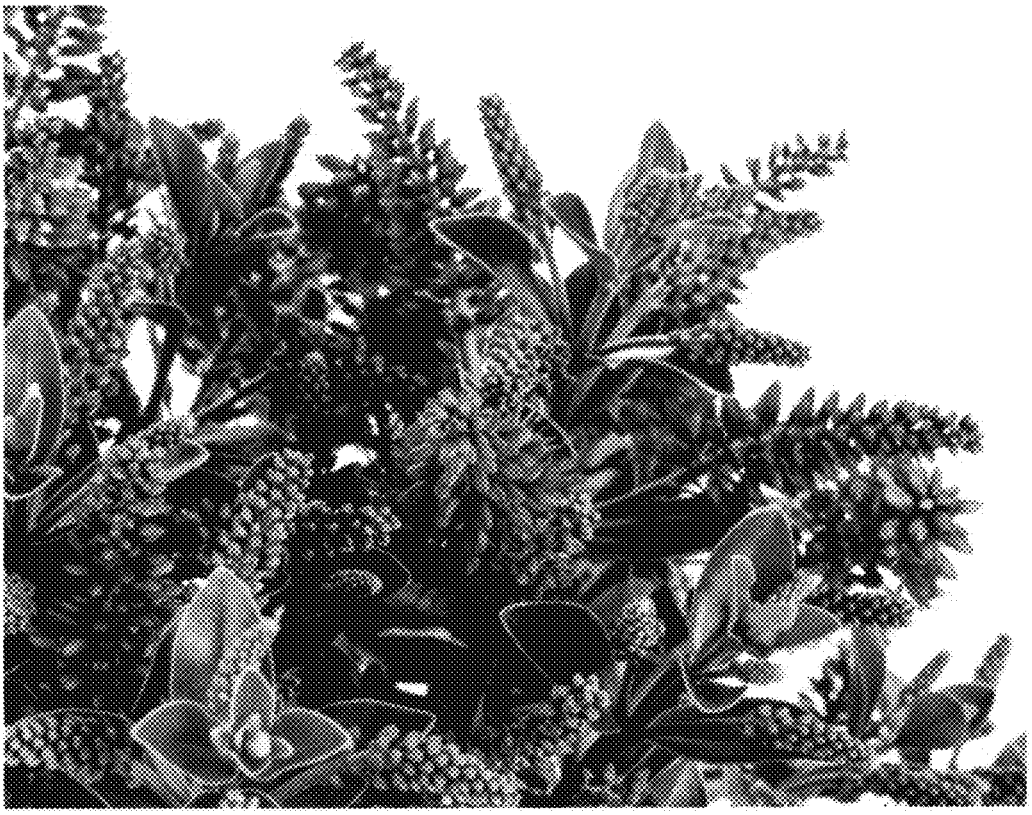

The photograph in FIG. 2 provides a close-up view of the inflorescences and foliage of 'HL1802019'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of 7-month-old plants of the new cultivar as grown outdoors in 12-cm containers in Wezep, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—An average of 5 weeks from summer into autumn in The Netherlands.

*Plant type.*—Evergreen shrub.

*Plant habit.*—Compact.

*Height and spread.*—Average of 17.4 cm in height (soil level to top of foliar plane), 18.2 cm (soil level to top of floral plane) and 21.5 cm in spread as a 7-month-old, reaches 70 cm in height and spread in the landscape.

*Cold hardiness.*—At least to U.S.D.A. Zone 8.

*Diseases and pests.*—Low susceptibility to leaf spot disease (*Septoria veronicae*) and downy mildew (*Perenospora* ssp.), no susceptibility or resistance to pests has been observed.

*Root description.*—Fibrous to slightly fleshy.

*Propagation.*—Softwood stem cuttings and tissue culture.

*Root development.*—3 to 4 weeks to initiate roots and 10 weeks to produce a young rooted plant.

*Growth rate.*—Moderate.

Branch description:

*Branch size.*—Lateral branches are an average of 13.4 cm in length and 2.5 mm in width.

*Branch shape.*—Round.

*Branch color.*—Young; 145A, tinged 177B, internodes; 200B, mature; 200C.

*Branch surface.*—Moderately glossy, densely covered with very short glandular hairs, 0.1 mm in length, matches surface color.

*Branch strength.*—Strong.

*Internode length.*—Average of 1.1 cm.

*Branching habit.*—Held in an average angle of 40° to vertical, average of 7 primary branches, 3 secondary branches.

Foliage description:

*Leaf shape.*—Narrow obovate, slightly carinate.

*Leaf division.*—Single.

*Leaf base.*—Cuneate.

*Leaf apex.*—Bluntly acute.

*Leaf venation.*—Pinnate, upper surface; 146B, lower surface; 147A to 147B.

*Leaf margins.*—Entire, slightly coarsely undulate.

*Leaf attachment.*—Sessile.

*Leaf arrangement.*—Opposite.

*Leaf surface.*—Both surfaces smooth, glabrous, non-rugose, upper surface moderately glossy, lower surface matte to very slightly glossy.

*Leaf color.*—Young upper surface; a blend of 137C and 143A, young lower surface; N77A and N186C, mature upper surface; NN137B, mature lower surface; 146B.

*Leaf number.*—Average of 10 per lateral branch 13 cm in length.

*Leaf size.*—An average of 2.6 cm in length and 1.4 cm in width.

Flower description:

*Inflorescence type.*—Raceme.

*Inflorescence size.*—Average of 5.2 cm in height and 1.9 cm in width.

*Inflorescence lastingness.*—About 7 days, self-cleaning.

*Flower shape.*—Campanulate.

*Flower fragrance.*—None.

*Flower quantity.*—Average 70 florets per inflorescence, 250 flowers per plant, 6,000 flowers and flower buds per plant.

*Flower arrangement.*—Axillary racemes.

*Flower aspect.*—Outward.

*Flower size.*—Average of 4 mm in height, 4 mm in diameter, 8 mm in depth, throat diameter 1.5 mm, flower tube length 2.5 mm, flower tube diameter 2 mm.

*Peduncles.*—Strong strength, 4.9 cm in length and about 1.25 mm in diameter, 146C in color, held at about a 45° angle to lateral branch, surface is matte and densely covered with very short glandular hairs an average of 0.1 mm in length, matches surface color.

*Pedicels.*—Moderately strong, average of 1.75 mm in length and 0.5 mm in diameter, held at about a 45° angle to peduncle, 146C in color.

*Flower buds.*—Narrow oblong to narrow elliptic, 4 mm in length and 1.75 mm in diameter, color; 86A, immature calyx 138B, surface is matte, smooth and glabrous.

*Calyx.*—Rotate-shaped, average of 2 mm in length and diameter.

*Sepals.*—4, 1 whorl, 2 mm in length, 0.8 mm in width, narrowly ovate in shape, entire margins, arrangement; rotate, narrowly acute tip, base cuneate and fused, surfaces dull and smooth, color: when opening and fully open upper surface; 143C, narrow margins 157A, when opening and fully open lower surface; 138B, narrow margins 145D.

*Petals.*—Average 4, 1 whorl, obovate in shape, base fused into campanulate shape, about 3.5 mm in length and 1.5 mm in width, entire and slightly concave margins, apex obtuse, upper and lower surface is smooth and glabrous, non-rugose, upper surface matte to very slightly glossy, lower surface very slightly glossy, color: upper surface when opening and fully open; N88B, lower surface when opening and fully open; N88B, top N88C, veins N81C, throat 83D, tube N88B.

*Floral Bracts.*—A single bract is placed below each individual flower, short oblong in shape, moderately concave, tip bluntly acute, cuneate base, 2 mm in length, 1 mm in width, both surfaces glabrous and 146C in color.

Reproductive organs:

*Gynoecium.*—Pistil; 1, 6 mm in length, stigma; club-shaped, 5 mm in length, N77C in color, style; 5.5 mm in length and N78A in color, ovary; 138B in color.

*Androecium.*—Stamens: 2, anthers; oblong in shape, 1 mm in length, 0.5 mm in width and 186D in color, filaments; 4 mm in length, color; 90D, pollen; none observed.

*Fruit and seed.*—None observed to date.

It is claimed:

1. A new and distinct cultivar of *Hebe* plant named 'HL1802019' as herein illustrated and described.

* * * * *